(12) United States Patent
Bouquerand et al.

(10) Patent No.: US 11,491,086 B2
(45) Date of Patent: Nov. 8, 2022

(54) PROCESS FOR RELEASING AN ACTIVE INGREDIENT

(71) Applicant: FIRMENICH SA, Satigny (CH)

(72) Inventors: Pierre-Etienne Bouquerand, Satigny (CH); Pascal Beaussoubre, Satigny (CH); Wolfgang Fieber, Satigny (CH); François Meyer, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/649,214

(22) PCT Filed: Dec. 13, 2018

(86) PCT No.: PCT/EP2018/084673
§ 371 (c)(1),
(2) Date: Mar. 20, 2020

(87) PCT Pub. No.: WO2019/115666
PCT Pub. Date: Jun. 20, 2019

(65) Prior Publication Data
US 2020/0297589 A1    Sep. 24, 2020

(30) Foreign Application Priority Data

Dec. 14, 2017  (EP) .................................... 17207334
Dec. 14, 2017  (EP) .................................... 17207498

(51) Int. Cl.
*A61K 8/02*  (2006.01)
*A61K 8/19*  (2006.01)
(Continued)

(52) U.S. Cl.
CPC .............. *A61K 8/0225* (2013.01); *A23L 2/39* (2013.01); *A23L 2/56* (2013.01); *A23L 2/68* (2013.01);
(Continued)

(58) Field of Classification Search
CPC .... A61K 8/0225; A61K 8/0283; A61K 8/062; A23L 2/39; A61Q 15/00; A61Q 13/00
See application file for complete search history.

(56) References Cited

U.S. PATENT DOCUMENTS 5,585,093 A * 12/1996 Murphy ............... A61K 8/0229
424/400
6,235,274 B1   5/2001 Lou et al.
(Continued)

FOREIGN PATENT DOCUMENTS

CN    104039395 A    9/2014
EP      2300146 B2    3/2017
(Continued)

OTHER PUBLICATIONS

Demineralization of water—DM water | Hard and Soft Water pp. 1-4. http://hardsoftwater.com/demineralization-of-water-dm-water/ Apr. 16, 2022 (Year: 2022).*
(Continued)

Primary Examiner — Lakshmi S Channavajjala
(74) Attorney, Agent, or Firm — Armstrong Teasdale LLP

(57) ABSTRACT

The present disclosure relates to delivery systems. More particularly, the present disclosure relates to a process for releasing an active ingredient including a step of contacting a powdered composition with a medium having a pH≤7. The powdered composition includes granules made of a water soluble polymer matrix, an oil phase dispersed in said matrix and carbonate particles. Consumer products such as an antiperspirant or deodorant composition or a powder soft drink beverage composition including the powdered composition are also object of the present disclosure.

14 Claims, 2 Drawing Sheets

(51) Int. Cl.
| | |
|---|---|
| *A23L 2/39* | (2006.01) |
| *A23L 2/56* | (2006.01) |
| *A23L 2/68* | (2006.01) |
| *A61K 8/06* | (2006.01) |
| *A61K 8/31* | (2006.01) |
| *A61K 8/362* | (2006.01) |
| *A61Q 15/00* | (2006.01) |

(52) U.S. Cl.
CPC ............ *A61K 8/0283* (2013.01); *A61K 8/062* (2013.01); *A61K 8/19* (2013.01); *A61K 8/31* (2013.01); *A61K 8/362* (2013.01); *A61Q 15/00* (2013.01)

(56) References Cited

U.S. PATENT DOCUMENTS

| | | | |
|---|---|---|---|
| 6,306,422 | B1 | 10/2001 | Batich et al. |
| 7,670,627 | B2 | 3/2010 | Shefer |
| 2004/0234597 | A1 | 11/2004 | Shefer |
| 2009/0252789 | A1* | 10/2009 | Trophardy ............... A23P 10/30 424/463 |
| 2013/0217789 | A1 | 8/2013 | Taylor |

FOREIGN PATENT DOCUMENTS

| | | | | |
|---|---|---|---|---|
| EP | 2579976 | B2 | 8/2017 | |
| GB | 716882 | * | 10/1954 | ............... 81/1 |
| WO | 2007004166 | A1 | 1/2007 | |
| WO | 2007054853 | A1 | 5/2007 | |
| WO | 2007111362 | A1 | 10/2007 | |
| WO | 2007135583 | A2 | 11/2007 | |
| WO | 2007137441 | A1 | 12/2007 | |
| WO | 2012082065 | A1 | 6/2012 | |
| WO | 2013057168 | A2 | 4/2013 | |
| WO | 2013092375 | A1 | 6/2013 | |
| WO | 2013174921 | A1 | 11/2013 | |
| WO | 2014044840 | A1 | 3/2014 | |
| WO | 2015091705 | A1 | 6/2015 | |
| WO | 2015110568 | A1 | 7/2015 | |
| WO | 2016054351 | A1 | 4/2016 | |
| WO | 2017134179 | A1 | 8/2017 | |

OTHER PUBLICATIONS

International Search Report and Written Opinion for corresponding PCT/EP2018/084673, dated Feb. 27, 2019, 12 Pages.

* cited by examiner

PROCESS FOR RELEASING AN ACTIVE INGREDIENT

This application is a U.S. National Phase application of PCT/EP2018/084673, filed Dec. 13, 2018, which claims priority to EP Application No. 17207498.1, filed on Dec. 14, 2017, and EP Application No. 17207334.8, filed on Dec. 14, 2017, the contents of which are hereby incorporated by reference in their entirety.

TECHNICAL FIELD

The present invention relates to delivery systems. More particularly, the present invention relates to a process for releasing an active ingredient comprising the step consisting of contacting a powdered composition with a medium having a pH≤7, wherein the powdered composition comprises granules made of a water soluble polymer matrix, an oil phase dispersed in said matrix and carbonate particles. Consumer products such as an antiperspirant or deodorant composition or a powder soft drink beverage composition comprising said powdered composition are also object of the present invention.

TECHNICAL BACKGROUND

Fragrances and flavors play an important role in the perception of consumer product performance and thus they often determine the consumer's choice for a given product. In addition, the increasing consumer demand for an intense and strong perfume or flavor deliver is driving the development of new delivery systems.

One main advantage of encapsulated fragrance/flavor is that fragrance/flavor performance and the blooming/long-lasting of the olfactive perception during and after application, (e.g. after rinsing and drying of the skin or the fabrics for fragrance) is enhanced.

The release of the hydrophobic active ingredient can be driven by different parameters such as the pH. Indeed, the controlled release of active ingredients through pH change is well-known in the literature.

US2004/0234597 and U.S. Pat. No. 7,670,627 disclose some solid hydrophobic nanospheres, entrapping a pharmaceutical active agent and encapsulated in a pH sensitive microsphere that dissolves under acidic conditions to release a pharmaceutical active ingredient on targeted cells. The solid nanospheres are formed of a wax material. The shell of the microsphere consists in a pH sensitive polymer.

Release of an active under more basic conditions can also be achieved. For example U.S. Pat. No. 6,306,422 describes how an active material can be entrapped in an hydrogel made of a polymer acrylic acid/methylmethacrylate in acidic conditions. The polymeric matrix swells under basic conditions of pH to allow the release of the active material in the surrounding medium.

Thermoresponsive components can be used in combination to pH responsive polymers to control the release of drugs or therapeutic agents, as described in US2013/0217789.

All pH trigger release solutions are based on the use of pH sensitive polymer (i.e. methacrylate) which have the drawback of delaying the release until the polymer starts to dissolve (negative pH trigger release) and the use of synthetic polymer even food-grade is not well perceived by consumers.

In view of the foregoing, there is need for a delivery system that could be used in different applications and that would display enhanced hydrophobic active ingredient release under acidic pH conditions.

The present invention is proposing a solution to the above-mentioned problem, based on the use of a powdered composition comprising granules made of a water soluble polymer matrix, an oil phase dispersed in said matrix and carbonate particles.

DRAWINGS

SUMMARY OF THE INVENTION

Figure 1:
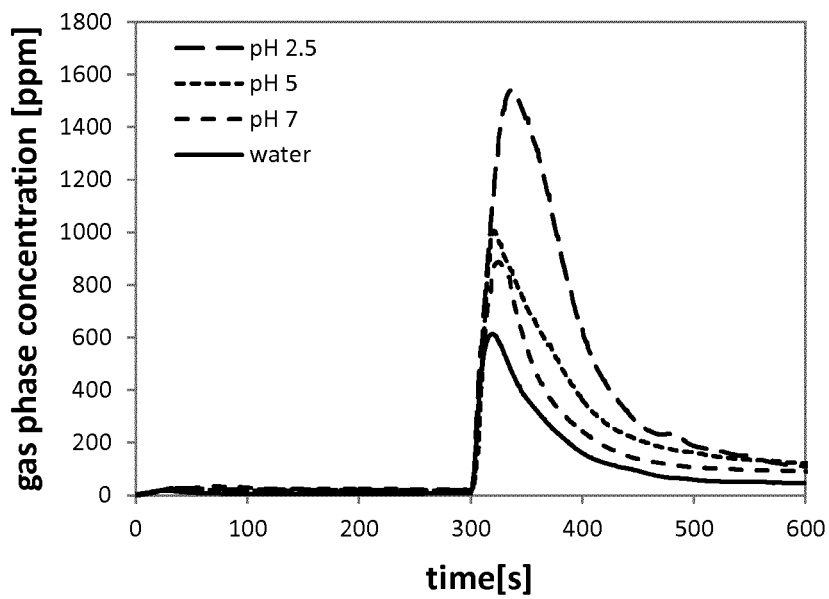
FIG. 1 represents experimental release curves of sample A in aqueous solutions at different pH.

Accordingly, the present invention relates to a process for releasing a hydrophobic active ingredient comprising the step consisting of contacting a powdered composition with a medium having a pH≤7, said powdered composition comprising granules, preferably spray-dried granules, made of:
- a water soluble polymer matrix,
- an oil phase comprising a hydrophobic active ingredient, preferably a perfume or a flavour, dispersed in said matrix, wherein said oil is at least partly not encapsulated in the matrix, and
- carbonate particles.

In a second aspect, the present invention relates to a composition comprising:
- an antiperspirant or deodorant active ingredient, and
- a powdered composition comprising granules, preferably spray-dried granules, made of:
  - a water soluble polymer matrix,
  - an oil phase comprising a hydrophobic active ingredient, dispersed in said matrix, wherein said oil is at least partly not encapsulated in the matrix, and wherein the hydrophobic active ingredient comprises a perfume, and
  - carbonate particles.

in the form of an antiperspirant or deodorant composition.

A third object of the invention is a composition comprising:
- an acidifying ingredient, and
- a dry flavouring ingredient, wherein said dry flavouring ingredient comprises a powdered composition comprising granules, preferably spray-dried granules, made of:
  - a water soluble polymer matrix,
  - an oil phase comprising a hydrophobic active ingredient, dispersed in said matrix, wherein said oil is at least partly not encapsulated in the matrix, and wherein the hydrophobic active ingredient comprises a flavour; and
  - carbonate particles.

in the form of a powder soft drink beverage composition.

DETAILED DESCRIPTION OF THE INVENTION

Unless stated otherwise, percentages (%) are meant to designate percent by weight of a composition.

When referring to "particles" or "powdered composition", percentages (%) are given for the dried composition.

According to the invention, "non-encapsulated oil" refers to oil that is simply entrapped (or freely dispersed) within the polymer matrix but that is not encapsulated in a microcapsule.

By contrast, according to the invention, "encapsulated oil" refers to oil that is encapsulated in a core-shell microcapsule.

A "core-shell microcapsule", or the similar, in the present invention it is meant that capsules have a particle size distribution in the micron range (e.g. a mean diameter (d(v, 0.5)) comprised between about 1 and 3000 µm, preferably between 1 and 500 µm, more preferably between 1 and 50 µm) and comprise an external polymeric shell and an internal continuous oil phase enclosed by the external shell. Coacervates are also part of the present invention.

According to an embodiment, non-encapsulated oil comprises a first hydrophobic active ingredient and the encapsulated oil comprises a second hydrophobic active ingredient that can be the same or can differ from the first hydrophobic active ingredient.

Carbonate particles used in the present invention are solid particles that are dispersible in water and serve as stabilizers, which accumulate at the interface between two immiscible liquids (typically denoted as oil and water phase) and stabilize droplets against coalescence. Such dispersions of two liquids stabilized by solid particles are referred to as Pickering emulsions. The most notable difference between a Pickering emulsion and a classical emulsion is that the former bears solid particles at the interface between two liquid phases serving as the stabilizing agent, whereas the latter uses molecular emulsifier to stabilize emulsions.

It has now been surprisingly found that a powdered composition prepared from a Pickering emulsion stabilized with carbonate particles could be used as a pH triggered delivery system since it shows a burst of active ingredient intensity, for example perfume or flavor intensity under acidic pH conditions. The powdered composition defined in the present invention exhibits higher performance compared to spray-dried powder obtained from emulsions stabilized with molecular emulsifiers.

According to the invention, the granules are not coated with solid particles. Indeed, it should be understood that once the granules are formed, solid carbonate particles are inside the granules at the interface between the oil phase and the water soluble matrix.

Process for Releasing a Hydrophobic Active Ingredient

A first object of the present invention is therefore a process for releasing a hydrophobic active ingredient comprising the step consisting of contacting a powdered composition with a medium having a pH≤7, said powdered composition comprising granules, preferably spray-dried granules, made of:
  a water soluble polymer matrix,
  an oil phase comprising a hydrophobic active ingredient, preferably a perfume or a flavour, dispersed in said matrix, wherein said oil is at least partly not encapsulated in the matrix, and
  carbonate particles.

According to an embodiment, the granules are spray-dried granules.

The powdered composition can be used as a pH triggered delivery system. According to the invention, a "pH triggered delivery system" is a delivery system that releases a hydrophobic active ingredient when triggered by a change in pH. More particularly, the powdered composition as defined in the present invention can be used as a pH triggered delivery system especially from a neutral/basic pH to an acidic pH (i.e ≤7). In other words, the delivery system defined in the present invention displays enhanced release under acidic pH conditions, preferably at a pH comprised between 2 and 7, more preferably between 2 and 6.

According to an embodiment, the medium is an aqueous medium.

According to an embodiment, the medium has a pH comprised between 2 and 7, more preferably between 2 and 6.

According to the invention, at least one part of the oil phase comprising a hydrophobic active ingredient is not encapsulated in core-shell microcapsules in the matrix.

Hydrophobic Active Ingredient

By "hydrophobic active ingredient", it is meant any active ingredient—single ingredient or a mixture of ingredients—which forms a two-phase dispersion when mixed with water.

In a preferred aspect of the invention, the hydrophobic active ingredient is defined by a log P above 1, more preferably above 2.

Preferably, the hydrophobic active ingredient comprises at least 90% by weight, relative to the total weight of the hydrophobic active ingredient, of compounds having a log P of at least 1, more preferably it comprises at least 90% by weight of ingredients having a log P of at least 2. Even more preferably, the hydrophobic active ingredient comprises at least 99% by weight, relative to the total weight of the hydrophobic active ingredient, of ingredients having a log P of at least 1, most preferably it comprises at least 99% by weight of ingredients having a log P of at least 2. For the purpose of the present invention log P is defined as the calculated log P as obtained by calculation using the EPI suite v3.10, 2000, U.S. Environmental Protection Agency.

In a preferred aspect of the invention, the hydrophobic active ingredient is selected from flavours and fragrances. For the purpose of the present invention, the terms "flavour or fragrance" encompass flavour or fragrance ingredients or compositions of current use in the flavour and/or fragrance industry, of both natural and synthetic origin. It includes single compounds and mixtures. Specific examples of such flavour or fragrance ingredients may be found in the current literature, e.g. in Fenaroli's Handbook of flavour ingredients, 1975, CRC Press; Synthetic Food adjuncts, 1947 by M. B. Jacobs, edited by Van Nostrand; or Perfume and Flavor Chemicals by S. Arctander, 1969, Montclair, N.J. (USA). Many other examples of current flavouring and/or perfuming ingredients may be found in the patent and general literature available. The flavouring or perfuming ingredients may be present in the form of a mixture with solvents, adjuvants, additives and/or other components, generally those of current use in the flavours and fragrance industry.

"Flavouring ingredients" are well known to a person skilled in the art of aromatising as being capable of imparting a flavour or taste to a consumer product, or of modifying the taste and/or flavour of said consumer product, or yet its texture or mouthfeel.

By "perfuming ingredients" it is understood here compounds which are used as active ingredients in perfuming preparations or compositions in order to impart a hedonic effect when applied to a surface. In other words, such compounds, to be considered as being perfuming ones, must be recognized by a person skilled in the art of perfumery as being able to impart or modify in a positive or pleasant way the odor of a composition or of an article or surface, and not just as having an odor. Moreover, this definition is also meant to include compounds that do not necessarily have an odor but are capable of modulating the odor of a perfuming composition, perfumed article or surface and, as a result, of modifying the perception by a user of the odor of such a composition, article or surface. It also contains malodor counteracting ingredients and compositions. By the term "malodor counteracting ingredient" we mean here compounds which are capable of reducing the perception of malodor, i.e. of an odor that is unpleasant or offensive to the human nose by counteracting and/or masking malodors. In a particular embodiment, these compounds have the ability to react with key compounds causing known malodors. The reactions result in reduction of the malodor materials' airborne levels and consequent reduction in the perception of the malodor.

Accordingly, in an embodiment, the hydrophobic active ingredient comprises at least 5 wt. %, preferably at least 10.%, preferably at least 20%, more preferably at least 30% and most preferably at least 40% of chemical compounds having a vapour pressure of at least 0.007 Pa at 25° C., preferably at least 0.1 Pa at 25° C., more preferably at least 1 Pa at 25° C. and most preferably at least 10 Pa at 25° C., all percentages being defined by weight relative to the total weight of the hydrophobic active ingredient. Compounds meeting these criteria are generally regarded as having a volatile character and therefore have an odor or flavour. The method of the present invention therefore allows efficient encapsulation of high amounts of volatile ingredients.

According to a particular embodiment, the hydrophobic active is a mixture of a perfume oil and a neutral carrier oil selected from cosmetically acceptable solvents or emollients such as silicon oils, mineral oils, alkanes, paraffin, triglycerides, fatty acids or gums, or mixture thereof. Examples of such products, but not limited to, are Neobee, Ester gum, Damar gum, isopropyl myristate or paraffins such as Gemseal.

According to a particular embodiment, the hydrophobic active is a mixture of a flavour oil and a neutral carrier oil selected from triglycerides, fatty acids or gums, or mixture thereof. Examples of such products, but not limited to, are Neobee, Ester gum, or Damar gum.

For the purpose of the present invention the vapour pressure is determined by calculation. Accordingly, the method disclosed in "EPI suite"; 2000 U.S. Environmental Protection Agency, is used to determine the value of the vapour pressure of a specific compound or component of the hydrophobic active ingredient.

The amount of hydrophobic active ingredient in the powdered composition is preferably comprised between 10 and 90% by weight, more preferably between 10 and 60% by weight, relative to the total weight of the powder.

According to an embodiment, the non-encapsulated hydrophobic active ingredient and the encapsulated hydrophobic active ingredient are identical.

According to an embodiment, the non-encapsulated hydrophobic active ingredient and the encapsulated hydrophobic active ingredient are different.

According to an embodiment, the oil phase does not comprise a polyphenol.

Water Soluble Polymer

Any water soluble biopolymer can be used for the purpose of the invention.

A "water soluble biopolymer" is intended for the purpose of the present invention as encompassing any biopolymer which forms a one-phase solution in water. Preferably, it forms a one phase solution when dissolved in water at concentrations as high as 20% by weight, more preferably even as high as 50% by weight. Most preferably it forms a one phase solution when dissolved in water at any concentration.

According to a particular embodiment, a water soluble biopolymer with a molecular weight below 100 KDa and devoid of emulsifying properties is used.

As "biopolymer devoid of emulsifying properties", it is intended for the purpose of the present invention polymers that are not surface active and are devoid of emulsifying properties with the oil phase. Suitable biopolymers devoid of emulsifying properties are soluble in water and are devoid of hydrophobic groups. Examples of biopolymers that are considered as having emulsifying properties and that are preferably excluded comprise pectin, gum Arabic, gelatin, modified starch such as octenylsuccinated starch E1450 (Capsul™, Hicap™, Puritygum™, Emcap™ etc.), modified cellulose such as ethylcellulose, hydroxypropylcellulose or hydroxypropylmethylcellulose. Such polymers are avoided because they would affect the particular release profile of volatiles from the granules of the present invention.

According to an embodiment, granules are free from molecular emulsifiers susceptible to form and/or stabilize an oil-in-water emulsion.

According to the invention, pectin, gum Arabic, gelatin, modified starch such as octenylsuccinated starch E1450 (Capsul™, Hicap™, Puritygum™, Emcap™ etc.), modified cellulose such as ethylcellulose, hydroxypropylcellulose or hydroxypropylmethylcellulose are considered as molecular emulsifiers.

According to a particular embodiment, the granules do not comprise gum Arabic.

According to a particular embodiment, the granules do not comprise gelatine.

According to a particular embodiment, the granules do not comprise modified starch.

According to a particular embodiment, the granules do not comprise modified cellulose.

Preferred water soluble biopolymers are biopolymers like polysaccharides, oligosaccharides and disaccharides. Preferred polysaccharides are starch hydrolysates with a dextrose equivalent above 2 and most preferred ones are selected from dextrins, maltodextrins, inulin, and cornsyrup. The most preferred biopolymer for use in the present invention is maltodextrin, preferable with a DE comprised between 1 and 19.

According to a particular embodiment, the water soluble biopolymer comprises, preferably consists of maltodextrin.

According to another embodiment, the water soluble biopolymer comprises maltodextrin and sucrose.

It is also particularly advantageous to use water soluble biopolymers which do not comprise any chemical substitution, meaning that the water soluble biopolymer has not been chemically (i.e. artificially) modified.

According to an embodiment, the amount of water soluble is comprised between 40 and 90%, preferably between 50 and 80%, based on the total weight of the powdered composition.

Once the granules are formed, the water-soluble matrix is dissolved in water upon application.

Carbonate Particles

Carbonate particles defined in the present invention are water-dispersible. By "water-dispersible", it means that they can form a dispersion in water but they are insoluble in water (pH>6).

A particle is considered as insoluble in water if its solubility is lower than 0.1% by weight.

The solid particles used in the present invention are carbonate particles, preferably inorganic, alkaline earth metal carbonates and encompasses all the polymorph forms.

More preferably, the solid carbonate particles are chosen in the group consisting of calcium carbonate, magnesium carbonate and mixture thereof.

In one embodiment, particles have an average diameter of at most 10 μm.

In another embodiment, particles have an average diameter of at most 9 μm.

In another embodiment, particles have an average diameter of at most 8 μm.

In another embodiment, particles have an average diameter of at most 7 μm.

In another embodiment, particles have an average diameter of at most 6 μm.

In another embodiment, particles have an average diameter of at most 5 μm.

In another embodiment, particles have an average diameter of at most 4 μm.

In another embodiment, particles have an average diameter of at most 3 μm.

In another embodiment, particles have an average diameter of at most 2 μm.

In another embodiment, particles have an average diameter of at most 1 μm.

Preferred particles are those having an average diameter of at most 1 μm, more preferably of at most 500 nm.

Preferred particles are those having an average diameter of at most 1 μm in one dimension to be absorbed at the oil/water interface and to stabilize oil droplets in water.

The relative ratio of solid carbonate particles, relative to the active substance is preferably comprised between 1:1 and 1:30, more preferably between 1:1.5 and 1:20, more preferably between 1:1.5 and 1:10, even more preferably from 1:1.5 to 1:6.

The granules of the invention may also comprise residual amounts of water, but typically less than 15%, preferably less than 10%, more preferably less than 2% by weight, relative to the total weight of the granules.

According to an embodiment, the ratio between the water soluble polymer matrix and the oil phase is from 95:5 to 50:50, preferably from 90:10 to 60:40.

Optional Acid

According to a particular embodiment, granules comprise an acid preferably chosen in the group consisting of ascorbic acid, citric acid, lactic acid, tannic acid, tartaric acid, malic acid, hydrochloric acid and mixtures thereof.

The acid can be dispersed within the granules or can be added as a coated layer on the granules.

The amount of acid is preferably comprised between 0.001:1 to 0.5:1, more preferably from 0.001:1 to 0.05:1, even more preferably from 0.005:1 to 0.05:1, relative to the amount of carbonate particles.

Microcapsules

According to an embodiment, the oil phase comprises at least one part that is encapsulated, preferably in an amount comprised between 0.25 and 30%, preferably between 0.5 and 20%, based on the total weight of the powdered composition.

Core-shell microcapsules defined in the present invention comprise a polymeric shell and an oil-based core comprising a hydrophobic active ingredient (that can be the same or different from the hydrophobic active ingredient of the non-encapsulated oil phase freely dispersed in the matrix).

The nature of the polymeric shell of the microcapsules of the invention can vary. As non-limiting examples, the shell can be made of a material selected from the group consisting of polyurea, polyurethane, polyamide, polyacrylate, polysiloxane, polycarbonate, polysulfonamide, urea formaldehyde, melamine formaldehyde resin, melamine formaldehyde resin cross-linked with polyisocyanate or aromatic polyols, melamine urea resin, melamine glyoxal resin, gelatin/gum arabic shell wall, and mixtures thereof.

According to a particular embodiment, the shell of the microcapsule is a hydrogel shell.

Examples of processes for the preparation of coacervates are for instance described in WO2013/174921, WO2014/044840, contents of which is also included by reference.

According to an embodiment, the shell of the microcapsule is based on melamine formaldehyde resin or melamine formaldehyde resin cross-linked with at least one polyisocyanate or aromatic polyols.

According to another embodiment, the shell of the microcapsule is polyurea-based.

The shell can also be a hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

According to a particular embodiment, the core-shell microcapsules are cross-linked melamine formaldehyde microcapsules obtainable by a process comprising the steps of:

1) admixing a perfume oil with at least a polyisocyanate having at least two isocyanate functional groups to form an oil phase;
2) dispersing or dissolving into water an aminoplast resin and optionally a stabilizer to form a water phase;
3) adding the oil phase to the water phase to form an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain a dried core-shell microcapsule;

This process is described in more details in WO 2013/092375 and WO 2015/110568, the contents of which are included by reference.

According to another embodiment the shell is polyurea-based made from, for example but not limited to isocyanate-based monomers and amine-containing crosslinkers such as guanidine carbonate and/or guanazole. Preferred polyurea-based microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to another embodiment, the shell is polyurethane-based made from, for example but not limited to polyisocyanate and polyols, polyamide, polyester, etc.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazole (all percentages being defined by weight relative to the total weight of the colloidal stabilizer).

According to another embodiment, the emulsifier is an anionic or amphiphilic biopolymer preferably chosen from the group consisting of polyacrylate (and copolymers especially with acrylamide), gum arabic, soy protein, gelatin, sodium caseinate and mixtures thereof.

According to a particular embodiment, the polyisocyanate is an aromatic polyisocyanate, preferably comprising a phenyl, a toluyl, a xylyl, a naphthyl or a diphenyl moiety. Preferred aromatic polyisocyanates are biurets and polyisocyanurates, more preferably a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N).

According to a particular embodiment, the polyisocyanate is a trimethylol propane-adduct of xylylene diisocyanate (commercially available from Mitsui Chemicals under the tradename Takenate® D-110N).

The preparation of an aqueous dispersion/slurry of core-shell microcapsules is well known from a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of:

1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c) a protic acid catalyst;
2) preparing an oil-in-water dispersion, wherein the droplet size is comprised between 1 and 600 um, and comprising:
   i. an oil;
   ii. a water medium
   iii. at least an oligomeric composition as obtained in step 1;
   iv. at least a cross-linker selected amongst
   A) $C_4$-$C_{12}$ aromatic or aliphatic di- or tri-isocyanates and their biurets, triurets, trimmers, trimethylol propane-adduct and mixtures thereof; and/or
   B) a di- or tri-oxiran compounds of formula A-(oxiran-2-ylmethyl)$_n$ wherein n stands for 2 or 3 and 1 represents a $C_2$-$C_6$ group optionally comprising from 2 to 6 nitrogen and/or oxygen atoms;
   v. optionally a $C_1$-$C_4$ compounds comprising two $NH_2$ functional groups;
3) heating said dispersion;
4) cooling said dispersion.

This process is described in more details in WO 2013/068255, the content of which is included by reference.

According to another embodiment, the shell of the microcapsule is polyurea- or polyurethane-based. Examples of processes for the preparation of polyurea- and polyurethane-based microcapsule slurry are for instance described in WO2007/004166, EP 2300146, EP2579976 the contents of which is also included by reference. Typically a process for the preparation of polyurea- or polyurethane-based microcapsule slurry include the following steps:
   a) dissolving at least one polyisocyanate having at least two isocyanate groups in an oil to form an oil phase;
   b) preparing an aqueous solution of an emulsifier or colloidal stabilizer to form a water phase;
   c) adding the oil phase to the water phase to form an oil-in-water dispersion, wherein the mean droplet size is comprised between 1 and 500 µm, preferably between 5 and 50 µm;
   d) applying conditions sufficient to induce interfacial polymerisation and form microcapsules in form of a slurry.

According to the invention, it should be understood that, after encapsulation, whatever the nature of the microcapsule(s), the internal core of the capsule is only made of the core oil composed of a perfume oil.

The granules defined in the present invention can contain microcapsules which can vary by the core perfume oil inside them and/or by the wall (different chemistries or same chemistries but different process parameters like cross-linking temperature or duration).

According to a particular embodiment of the invention, the microcapsules have an outer coating selected from the group consisting of a non-ionic polysaccharide, a cationic polymer and mixtures thereof.

Such coating will help drive capsule deposition and retention on substrate during the wash process so that a significant part of the capsules which have not been broken in the wash phase/upon lathering would transfer to the substrate (skin, hair fabrics) and be available for perfume release when the capsules are broken upon rubbing after drying.

Non-ionic polysaccharide polymers are well known to a person skilled in the art. Preferred non-ionic polysaccharides are selected from the group consisting of locust bean gum, xyloglucan, guar gum, hydroxypropyl guar, hydroxypropyl cellulose and hydroxypropyl methyl cellulose.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 2M Dalton, more preferably between 50,000 and 3.5M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

Process for the Preparation of the Powdered Composition

There are several alternatives to the method for the preparation of the powdered composition as defined in the invention.

Indeed, there is no limitation regarding the way to obtain the dried particles.

Among those methods, one may cite for example the spray-drying that is well-known method for the encapsulation of active ingredient.

However, one may cite also other drying method such as the extrusion, the fluidized bed, or even a drying at room temperature using materials (carrier, desiccant) that meet specific criteria (see for example WO2017134179).

According to an embodiment, granules are obtainable and/or obtained by a process comprising the steps of:
a) adding a solution of a water-soluble polymer to a Pickering emulsion, wherein the Pickering emulsion comprises
 i. a non-encapsulated oil phase comprising a hydrophobic active ingredient, preferably a perfume or a flavour;
 ii. carbonate particles; and
 iii. water;
b) optionally, adding a core-shell microcapsule slurry to the emulsion of step a), said slurry comprising microcapsules having a polymeric shell and a core comprising an encapsulated oil; and
c) drying the emulsion obtained in step a) or b) to obtain a powdered composition.

According to a particular embodiment, granules are spray-dried granules and are obtainable and/or obtained by a process comprising the steps of:
a) adding a solution of a water-soluble polymer to a Pickering emulsion, wherein the Pickering emulsion comprises
 i. a non-encapsulated oil phase comprising a hydrophobic active ingredient, preferably a perfume or a flavour;
 ii. carbonate particles; and
 iii. water;
b) optionally, adding a core-shell microcapsule slurry to the emulsion of step a), said slurry comprising microcapsules having a polymeric shell and a core comprising an encapsulated oil; and
c) spray-drying the emulsion obtained in step a) or b) to obtain a powdered composition.

All components for the process are as defined above for the granules.

Step a): Adding a Solution of a Water-Soluble Polymer to a Pickering Emulsion

The amount of the hydrophobic active ingredient in the Pickering emulsion is preferably comprised between 5 and 67% by weight, more preferably between 10 and 40% by weight, relative to the total weight of the emulsion.

In another preferred embodiment, the solid carbonate particles are present in an amount of from 0.1 to 30%, preferably from 0.5 to 30% more preferably from 1 to 16% by weight, relative to the total weight of the Pickering emulsion.

In a preferred aspect of the invention, the amount of water in the emulsion is comprised between 20 and 80% by weight, relative to the total weight of the Pickering emulsion.

According to a particular embodiment, an acid preferably chosen in the group consisting of ascorbic acid, citric acid, lactic acid, tannic acid, tartaric acid, malic acid, hydrochloric acid and mixtures thereof is added in the process.

According to an embodiment, the acid is added in step a) when preparing the emulsion.

According to another embodiment, once the powdered composition is formed, the acid is blended with the powder.

The amount of acid is preferably comprised between 0.001:1 to 0.5:1, more preferably from 0.001:1 to 0.05:1, even more preferably from 0.005:1 to 0.05:1, relative to the amount of carbonate particles. Depending on the acid added in emulsion, the amount is such that particles are not solubilized. The addition of acid can help in stabilizing oil droplets by carbonate particles, and can increase the encapsulation yield.

The emulsion can be formed using any known emulsifying method, such as high shear mixing, sonication or high pressure homogenization. Such emulsifying methods are well known to the person skilled in the art.

According to an embodiment, no molecular emulsifier susceptible to form and/or stabilize an oil-in-water emulsion is added at any stage of the process.

The droplet size d(v,0.9) of the emulsion is preferably comprised between 0.5 and 20 μm, more preferably between 0.5 and 15 μm.

According to the invention, the solid particle is water-dispersible, i.e. it disperses easily in water to form a homogeneous suspension of particles. Preferably, in the emulsion, the particle will form with the oil and the water a contact angle $\theta \leq 90°$, more preferably $10° \leq \theta \leq 90°$. The contact angle $\theta$ is the three-phase contact angle, measured through the aqueous phase, that is made by an interface of water and oil on the particle's surface. Practically, when the contact angle is comprised within the above range the particle succeeds in stabilizing an oil in water emulsion. It is well-known in the field of colloids that the contact angle is a quantification of the wettability of the particles at an interface oil/water. A more detailed definition of the contact angle can be found in Dickinson, E., *Use of nanoparticles and microparticles in the formation and stabilization of food emulsions*, Trends in Food Science & Technology (2011).

The emulsion may also contain optional ingredients. It may in particular further contain an effective amount of a fireproofing or explosion suppression agent. The type and concentration of such agents in spray-drying emulsions is known to the person skilled in the art. One can cite as non-limiting examples of such fireproofing or explosion suppression agents inorganic salts, $C_1$-$C_{12}$ carboxylic acids, salts of $C_1$-$C_{12}$ carboxylic acids and mixtures thereof. Preferred explosion suppression agents are, salicylic acid, acetic acid, propionic acid, butyric acid, isobutyric acid, valeric acid, caproic acid, citric acid, succinic acid, hydroxysuccinic acid, maleic acid, fumaric acid, oxylic acid, glyoxylic acid, adipic acid, lactic acid, tartaric acid, ascorbic acid, the potassium, calcium and/or sodium salts of any of the aforementioned acids, and mixtures of any of these.

Other optional ingredients include antioxidants, preservatives, colorants and dyes. According to the invention, the carbonate particles are insoluble in water prior the emulsification step.

To that end, the water phase in which carbonate particles are dispersed prior to emulsification needs to be at a given pH, typically greater than 6 to limit the solubilization of the particles and allow the solid-stabilized emulsion to be formed. One may add for example to the dispersion a pH buffer such as $KH_2PO_4/K_2HPO_4$ to increase the pH if the pH of the dispersion is lower than 6.

The water soluble biopolymer is added in an amount between 5 to 75% by weight, more preferably between 10 and 55% by weight, relative to the total weight of the mixture obtained in step a). These concentrations are defined so as to maintain the viscosity of the mixture below 400 Pa, which is a preferred range of viscosity in spray-drying processes.

The addition of the different components to form the oil-in-water emulsion in step a) can be performed in different order. According to one embodiment, step a) comprises the following steps:

(i) Optionally, buffering the water to the desired pH (>6)
(ii) Dispersing carbonate particles in water
(iii) Adding the oil phase to the suspension and emulsifying
(iv) Adding the water soluble polymer to the oil-in-water emulsion.

According to another embodiment, step a) comprises the following steps:

(i) Optionally, buffering the water to the desired pH (>6)
(ii) Dispersing carbonate particles in water
(iii) Adding the water soluble polymer to the water dispersion
(iv) Adding the oil phase to the suspension and emulsifying.

Step b): Adding a Microcapsule Slurry

Microcapsules that can be added are as defined above for the granules.

This embodiment is particularly suitable when a dual type of release is desired. For example, one may desire firstly an initial strong burst of perfume (during a washing step for example) followed by a long term release.

Preferably, the amount of oil in microcapsules added in step b) represents from 1/50 to 1/2, more preferably from 1/20 to 1/2, even more preferably from 1/10 to 1/3 relative to the oil emulsified and non-encapsulated.

Step c): Spray-Drying

In step c), the emulsion comprising non encapsulated oil and optionally encapsulated oil is spray-dried so as to obtain granules.

The emulsion is first subjected to a spraying step during which the emulsion is dispersed in the form of drops into a spraying tower. Any device capable of dispersing the emulsion in the form of drops can be used to carry out such dispersion. For instance, the emulsion can be guided through a spraying nozzle or through a centrifugal wheel disk. Vibrated orifices may also be used.

In one aspect of the invention the emulsion is dispersed in the form of drops into a cloud of powdering agent present in the dry tower. Such type of process is for example described in details in WO2007/054853 or in WO2007/135583.

For a specific formulation, the size of the granules is influenced by the size of the drops that are dispersed into the tower. When a spraying nozzle is used for dispersing the drops, the size of such drops can be controlled by the flow rate of an atomising gas through the nozzle, for example. In the case where a centrifugal wheel disk is used for dispersal, the main factor for adjusting droplet size is the centrifugal force with which the drops are dispersed from the disk into the tower. The centrifugal force, in turn, depends on the speed of rotation and the diameter of the disk. The feed flow rate of the emulsion, its surface tension and its viscosity are also parameters controlling the final drop size and size distribution. By adjusting these parameters, the skilled person can control the size of the drops of the emulsion to be dispersed in the tower.

Once sprayed in the chamber, the droplets are dried using any technique known in the art. These methods are perfectly documented in the patent and non-patent literature in the art of spray-drying. For example, Spray-Drying Handbook, $3^{rd}$ ed., K. Masters; John Wiley (1979), describes a wide variety of spray-drying methods.

The process of the present invention may be performed in any conventional spraying tower. A conventional multi-stage drying apparatus is for example appropriate for conducting the steps of this process. It may comprise a spraying tower, and, at the bottom of the tower, a fluidised bed intercepting partially dried granules after falling through the tower.

The amount of flavour or fragrance lost during the spray drying step is preferably below 15%, more preferably below 10%, most preferably below 5%, these percentages being defined by weight, relative to the theoretical amount that would be present in the granules if there was absolutely no flavour or fragrance lost during the spray-drying step.

In a preferred aspect of the invention the size of the granules is typically of at least 10 µm, preferably at least 20 µm. Depending on the process used for spray-drying, in particular when a powdering agent is present in the drying tower, as described above, the dry granules can have an average size of up to 300 or even up to 750 µm. In a preferred embodiment of the invention, the average size of the granules is at least 5 times larger than the average size of the oil droplets in the emulsion.

Antiperspirant or Deodorant Composition

The granules defined in the present invention have shown a boost of perfume intensity under acidic pH conditions. Therefore, they may be incorporated into any antiperspirant or deodorant product. Indeed, without being bound by any theory, once applied onto the skin, the acidic pH of the human sweat solubilize the particles, inducing the coalescence of the oil droplets and the release of the perfume.

Thus, another object of the invention is a composition comprising:
an antiperspirant or deodorant active ingredient, and
a powdered composition comprising granules, preferably spray-dried granules, made of:
a water soluble polymer matrix,
an oil phase comprising a hydrophobic active ingredient, dispersed in said matrix, wherein said oil is at least partly not encapsulated in the matrix, and wherein the hydrophobic active ingredient comprises a perfume;

carbonate particles, in the form of an antiperspirant or deodorant composition.

As used herein, the term "antiperspirant or deodorant product" refers to the normal meaning in the art; i.e. a composition applied on skin allowing to reduce or prevent body odour.

Exemplary products include wax-based sticks, soap-based sticks, compressed powder sticks, roll-on suspensions or solutions, emulsions, gels, creams, squeeze sprays, pump sprays, aerosols, and the like. Each product form may contain its own selection of additional components, some essential and some optional. The types of components typical for each of the above product forms may be incorporated in the corresponding compositions presented herein.

Antiperspirant or deodorant active ingredients are preferably incorporated in an amount of from 0.5-50%, particularly from 5 to 30% of the weight of the composition.

Antiperspirant or deodorant active ingredients may include astringent metallic salts, especially inorganic and organic salts of aluminum, zirconium and zinc, as well as mixtures thereof. Even more specifically, antiperspirant actives or deodorant active ingredients may be selected from the group consisting of aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY and aluminum zirconium trichlorohydrate GLY.

Granules defined in the present invention are preferably incorporated in an amount of from 0.4% to 10%, particularly from 0.4% to 5%, more preferably from 0.4% to 2% of the weight of the composition.

Free perfume can be added in an amount comprised between 0.1 and 8%, preferably between 0.1 and 4% by weight based on the total weight of the composition.

Depending of the type of product, the deodorant or antiperspirant product may comprise supplementary ingredients enabling to obtain the desired form. Non-limiting examples of suitable ingredients include emollient(s), solubilizer(s), antioxidant(s), preservative(s), carrier(s), odour entrapper(s), propellant(s), primary structurant(s), additional chassis ingredient(s), volatile silicone solvent(s), gellant(s), buffering agent and residue masking material(s). A person skilled in the art is able to select them on the basis of its general knowledge and according to intended form of the deodorant or antiperspirant composition.

For example, by way of illustration, a roll-on deodorant or antiperspirant product may comprise water, emollient, solubilizer, antioxidants, preservatives, or combinations thereof; a clear gel product or antiperspirant product may comprise water, emollient, solubilizer, malodour-absorbing material, antioxidants, preservatives, ethanol, or combinations thereof; a body spray may contain a carrier, odour entrappers, propellant, or combinations thereof; an invisible solid deodorant or antiperspirant product may contain a primary structurant, and additional chassis ingredient(s); a soft solid deodorant or antiperspirant product may comprise volatile silicone, gellant, residue masking material, or combinations thereof; an aerosol deodorant or antiperspirant product may comprise a carrier, a propellant, or a combination thereof.

Emollients suitable for deodorant or antiperspirant products include, but are not limited to, propylene glycol, polypropylene glycol (like dipropylene glycol, tripropylene glycol, etc.), diethylene glycol, triethylene glycol, neopentyl glycol diheptanoate, PEG-4, PEG-8, 1,2-pentanediol, 1,2-hexanediol, hexylene glycol, glycerin, $C_2$ to $C_{20}$ monohydric alcohols, $C_2$ to $C_{40}$ dihydric or polyhydric alcohols, alkyl ethers of polyhydric and monohydric alcohols, dicaprylyl carbonate, dicaprylyl ether, diethylhexylcyclohexane, dibutyl adipate, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

The composition of the invention can include any topical material that is known or otherwise effective in preventing or eliminating malodour, including malodour associated with sweat and/or perspiration. Suitable material may be selected from the group consisting of antimicrobial agents (e.g., bacteriocides, fungicides), malodour-absorbing material, and combinations thereof.

Antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof. Suitable solubilizers include, for example, polyethylene glycol ether of Cetearyl Alcohol, hydrogenated castor oil such as polyoxyethylene hydrogenated castor oil, polyoxyethylene 2 stearyl ether, polyoxyethylene 20 stearyl ether, and combinations thereof.

Suitable preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathan® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name German® II from Sutton Laboratories, Inc.; N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, German 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

Suitable carriers can include, water, alcohol, or combinations thereof. Useful alcohols include $C_1$-$C_3$ alcohols. In some aspects, the alcohol is ethanol.

Some examples of propellants include compressed air, nitrogen, inert gases, carbon dioxide, and mixtures thereof. Propellants may also include gaseous hydrocarbons like propane, n-butane, isobutene, cyclopropane, and mixtures thereof; e.g. A-46 (a mixture of isobutane, butane and propane), A-31 (isobutane), A-17 (n-butane), A-108 (propane), AP70 (a mixture of propane, isobutane and nbutane), AP40 (a mixture of propane, isobutene and n-butane), AP30 (a mixture of propane, isobutane and n-butane). Some non-limiting examples of propellants include 1,1-difluoroethane, 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof.

The term "primary structurant" as used herein means any material known or otherwise effective in providing suspending, gelling, viscosifying, solidifying, and/or thickening properties to the composition or which otherwise provide structure to the final product form. These primary structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof. Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides; behenyl alcohol, or combinations thereof.

Chassis ingredients may be an additional structurant such as stearyl alcohol and other fatty alcohols; hydrogenated castor wax (e.g., Castorwax MP80, Castor Wax, etc.);

hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof; non-volatile organic fluids such as mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate or isobutyl stearate; clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Volatile silicone solvents suitable for use in the antiperspirant compositions include, but are not limited to, solvent such as Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

The gellant material may comprise saturated or unsaturated, substituted or unsubstituted, fatty alcohols or mixtures of fatty alcohols having from about 20 to about 60 carbons atoms, alternatively from about 20 to about 40 carbon atoms. In some embodiments, the gallant materials comprise combinations of the fatty alcohols. In some embodiments, the fatty alcohol gellants are may be saturated, unsubstituted monohydric alcohols or combinations thereof, which have a melting point of at less than about 110° C., alternatively from about 60° to about 110° C., alternatively between about 100° C. and 110° C.

Specific examples of fatty alcohol gellants for use in the antiperspirant products that are commercially available include, but are not limited to, Unilin® 425, Unilin® 350, Unilin® 550 and Unilin® 700 (supplied by Petrolite).

A suitable buffering agent may be alkaline, acidic or neutral. The buffer may be used in the composition or product for maintaining the desired pH. Suitable buffering agents include, for example, hydrochloric acid, sodium hydroxide, potassium hydroxide, and combinations thereof.

Non-limiting examples of suitable residue masking materials for use in the antiperspirant products include butyl stearate, diisopropyl adipate, petrolatum, nonvolatile silicones, octyldodecanol, phenyl trimethicone, isopropyl myristate, $C_{12-15}$ ethanol benzoates and PPG-14 Butyl Ether.

The deodorant or antiperspirant products disclosed herein may comprise other optional ingredients such as emulsifiers, distributing agents, antimicrobials, pharmaceutical or other topical actives, surfactants, and the like.

The nature, amount and type of ingredients does not warrant a more detailed description here, which in any case would not be exhaustive, the skilled person being able to select them on the basis of its general knowledge and according to intended form.

In some aspects, the composition comprises less than 95 wt % of water, relative to the total weight of the composition. In some aspects, the composition comprises less than 90 wt % of water, relative to the total weight of the composition. In some aspects, the composition comprises less than 85 wt % of water, relative to the total weight of the composition. In some aspects, the composition comprises less than 80 wt % of water, relative to the total weight of the composition. In some aspects, the composition comprises less than 75 wt % of water, relative to the total weight of the composition. In some aspects, the composition comprises less than 70 wt % of water, relative to the total weight of the composition. In some aspects, the composition comprises less than 65 wt % of water, relative to the total weight of the composition. In some aspects, the composition comprises less than 60 wt % of water, relative to the total weight of the composition. In some aspects, the composition comprises less than 55 wt % of water, relative to the total weight of the composition. In some aspects, the composition comprises less than 50 wt %, or less than 40 wt %, or less than 30 wt %, or less than 20 wt %, or less than 10 wt % of water, relative to the total weight of the deodorant or antiperspirant composition. In some aspects, the composition is water-free.

Powder Soft Drink Beverage Composition

The granules defined in the present invention can also show a burst of flavor intensity under acidic pH conditions. Therefore, they may be incorporated into any powder soft drink beverage comprising an acidifying ingredient.

Powder soft drink is a powder designed to mix usually with water to produce a beverage resembling fruit juice or flavored soft drink.

Therefore, another object of the invention is a composition comprising:
- an acidifying ingredient, and
- a dry flavouring ingredient comprising the powdered composition as defined above, wherein the hydrophobic active ingredient comprises a flavour;
in the form of a powder soft drink beverage composition.

Upon dilution of the powder soft drink beverage composition in water, the pH of the beverage composition is acidic (typically below pH=6) and a burst of the release flavor is perceived by the consumer According to a particular embodiment, the powder soft drink further comprises at least one ingredient chosen in the group consisting of a dry sweetening ingredient; a sweetener; a coloring ingredient; mouthfeel agents such as carboxymethyl cellulose or pectin; clouding agents; buffering agent; vitamins; nutrients; and mixtures thereof.

Powder soft drink mixture is preferably incorporated in water in an amount between 5 to 30%, preferably around 12% but the dilution could be easily adjusted to the consumer preferences. Alternatively the powder soft drink mixture can be used to flavor other liquid like milk.

Granules defined in the present invention are preferably incorporated in an amount of from 0.01-2%, particularly from 0.05 to 0.5% of the weight of the powder soft drink beverage composition.

The powder soft drink can be packaged as unit doses but is of course not limited to this type of packaging.

The invention will now be further described by way of examples. It will be appreciated that the invention as claimed is not intended to be limited in any way by these examples.

EXAMPLES

Example 1

Powdered Composition According to the Invention

In a 200 ml beaker, 1.14 g of a precipitated $CaCO_3$ suspension 70% was weighed. The suspension was completed to 80 g with deionized Water buffered to pH7. 20 g of limonene was then added to the suspension, the beaker was placed in an ice bath and the solution was emulsified for 2 min. using an ultrasonic probe (sonotrode H14 tip 14) connected on a Hielscher UP400S ultrasonic processor. Average droplet size was checked to be around 5 μm using microscopy. Emulsion 1 is obtained (see table 1 below).

TABLE 1

| Composition of emulsion 1 | |
|---|---|
| Compound | Emulsion 1 (%) |
| $CaCO_3$ [1] | 0.8 |
| Limonene oil [2] | 20 |
| Water pH 7 | 79.2 |
| TOTAL | 100 |

[1] Albafil S10 ®, Origin: Specialty Minerals Inc.
[2] Limonene 1x dist, Origin: Firmenich SA, Switzerland To 50 g of the previous emulsion, 70 g of a Maltodextrin18DE (50% solution) was added to get the spray feed solution 1 (see table 2 below). The pH was adjusted to around 7 using NaOH 2M.

TABLE 2

| Composition of spray feed solution 1 | |
|---|---|
| Compound | Spray feed solution 1 (%) |
| $CaCO_3$ | 0.33 |
| Limonene oil | 8.33 |
| Maltodextrin [3] | 29.17 |
| Water | 62.17 |
| TOTAL | 100 |

[3] Glucidex ®18DE (origin: Roquette)

Spray-drying was performed using a Büchi B-290. Entrance temperature was measured at 180° C., while the temperature at the exit was between 86° C. and 97° C.

A yield in atomization of about 54.5% was achieved. The final powder granules were composed exclusively of $CaCO_3$ particles, Maltodextrin 18DE and traces of salts used for buffering for the solid matrix, and were loaded with about 12% of limonene (see table 3).

TABLE 3

| Composition of the powdered composition 1 | |
|---|---|
| Compound | Powdered composition 1 (%) |
| $CaCO_3$ | 0.94 |
| Limonene oil | 12 |
| Maltodextrin | 82.36 |
| Water | 4.70 |
| TOTAL | 100 |

Example 2

Powdered Composition According to the Invention

A similar example to Example 1 has been carried out but by adjusting to a different pH.

To 50 g of the previous emulsion 1, 70 g of a Maltodextrin18DE (50% solution) was added to get the spray feed solution. The pH was adjusted to around 8.5 using NaOH 2M.

Spray-drying was performed using a Büchi B-290. Entrance temperature was measured at 180° C., while the temperature at the exit was between 86° C. and 97° C.

A yield in atomization of about 57.8% was achieved. The final powder granules were composed exclusively of $CaCO_3$ particles, Maltodextrin 18DE and traces of salts used for buffering for the solid matrix, and were loaded with about 12.7% of limonene.

Example 3

Powdered Composition According to the Invention

A similar example to Example 1 has been carried out but by using a higher amount of $CaCO_3$ particles.

In a 200 ml beaker, 8 g of a precipitated $CaCO_3$ suspension 70% was weighed. The suspension was completed to 80 g with deionized Water buffered to pH7. 20 g of limonene was then added to the suspension, the beaker was placed in an ice bath and the solution was emulsified for 2 min. using an ultrasonic probe (sonotrode H14 tip 14) connected on a Hielscher UP400S ultrasonic processor. Average droplet size was checked to be around 5 µm using microscopy.

TABLE 4

Composition of emulsion 2

| Compound | Emulsion 2 (%) |
| --- | --- |
| $CaCO_3$ [1] | 5.6 |
| Limonene oil [2] | 20 |
| Water | 74.4 |
| TOTAL | 100 |

[1] Albafil S10 ®, Origin: Specialty Minerals Inc.
[2] Limonene 1x dist, Origin: Firmenich SA, Switzerland To 50 g of the previous emulsion, 70 g of a Maltodextrin18DE (50% solution) was added to get the spray feed solution 2 (see table 5). The pH was adjusted to around 7 using NaOH 2M.

TABLE 5

Composition of spray feed solution 2

| Compound | Spray feed solution 2 (%) |
| --- | --- |
| $CaCO_3$ | 2.33 |
| Limonene oil | 8.33 |
| Maltodextrin [3] | 29.17 |
| Water | 60.17 |
| TOTAL | 100 |

[3] Glucidex ®18DE (origin: Roquette)

Spray-drying was performed using a Büchi B-290. Entrance temperature (Inlet T°) was measured at 180° C., while the temperature at the exit (outlet T°) was between 86° C. and 97° C.

A yield in atomization of about 51.15% was achieved. The final powder granules were composed exclusively of $CaCO_3$ particles, Maltodextrin 18DE and traces of salts used for buffering for the solid matrix, and were loaded with about 10.7% of limonene.

TABLE 6

Composition of the powdered composition 2

| Compound | Powdered composition 1 (%) |
| --- | --- |
| $CaCO_3$ | 6.29 |
| Limonene oil | 10.7 |
| Maltodextrin | 78.61 |
| Water | 4.4 |
| TOTAL | 100 |

Example 4 pH Triggered Release Performance

Samples were prepared according to procedure from Example 1 (see composition in table below).

TABLE 7

Composition of the powdered composition 4 and comparative powder X

| | Powdered composition 4 Sample A | Comparative powdered Sample X |
| --- | --- | --- |
| $CaCO_3$ [1] | 6 | 0 |
| Limonene [2] | 21 | 35 |
| Maltodextrin [3] | 73 | 58.5 |
| Modified Starch [4] | 0 | 6.5 |

[1] Albafil S10 ®, Origin: Specialty Minerals Inc.
[2] Limonene1X dist Fab, origin: Firmenich SA, Switzerland
[3] Glucidex ®18DE (origin: Roquette)
[4] Capsul ®, origin Ingredion The release of volatile limonene after dissolution of sample A and sample X in water was monitored with a portable photoionization detector (Model Tiger, Ion-Science).

Between 50 mg and 100 mg of the spray-dried powder was mixed with maltodextrin MD 18 DE in a ratio of 1:3 in order to ensure a proper, complete and instantaneous dispersion of the powder once in contact with water. The total quantity of encapsulated limonene was equal in all experiments. The samples were placed into the headspace cell, the cell was closed and the detector was connected to the air outlet. The headspace concentration was measured continuously at intervals of 1 second. After equilibration of 5 minutes 10 mL of water or buffer solution was added through a septum and simultaneously stirring was started. The headspace was measured for another five minutes.

After an initial burst phase of volatile release that typically lasts for about 60 seconds the signal quickly drops to a plateau value, followed by an exponential decay until complete evaporation of the volatile. The maximum volatile concentration in the gas phase after dilution was determined for each sample.

TABLE 8 volatile concentration in the gas phase after dilution

| Dissolution medium | pH | Sample A gas concentration [ppm] | Sample X gas concentration [ppm] |
| --- | --- | --- | --- |
| water | | 614 | 186 |
| 1M phosphate buffer | 7 | 887 | 157 |

TABLE 8-continued volatile concentration in the gas phase after dilution

| Dissolution medium | pH | Sample A gas concentration [ppm] | Sample X gas concentration [ppm] |
|---|---|---|---|
| 1M phosphate buffer | 5 | 1006 | 157 |
| 1M citrate buffer | 2.5 | 1541 | 217 |

Figure 2:
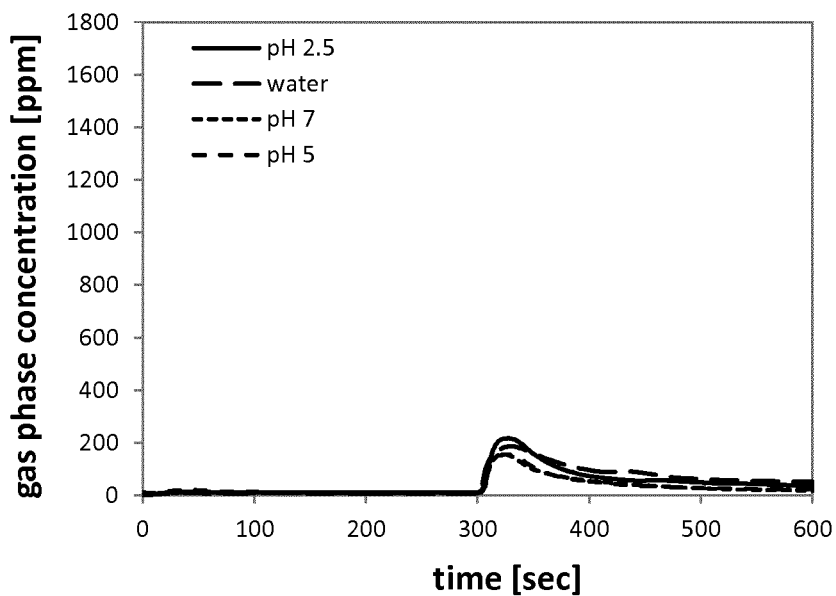
FIG. 2 represents experimental release curves of sample X in aqueous solution at different pH.

The spray dried emulsion according to the invention: sample A (see FIG. 1) shows systematically higher gas phase concentrations than the comparative sample X (see FIG. 2). In addition, the gas phase concentration increased significantly when the pH of the dissolution medium decreased. Compared to pure water (final pH 8.8) the gas phase concentration increased by a factor of 2.5 when using a citrate buffer at pH 2.5. In contrast, no pH effect could be observed for the comparative spray dried emulsion.

Example 5 pH Triggered Release Performance

Samples were prepared according to procedure from Example 1 (see composition in table below).

TABLE 8

Composition of the powdered compositions

| | Powdered composition 5 Sample B | Comparative Sample Y | Comparative Sample Z |
|---|---|---|---|
| $CaCO_3$ [1] | 9.05 | 0 | 0 |
| Silica [2] | 0 | 1.96 | 0 |
| Orange oil [3] | 27.15 | 29.35 | 30 |
| Modified starch [4] | 0 | 0 | 10 |
| Maltodextrin [5] | 63.35 | 68.5 | 60 |
| Ascorbic acid [6] | 0.45 | 0 | — |
| Citric acid [7] | — | 0.19 | — |

[1] Vicality Albafil 10 (origin Speciality Minerals Inc. USA)
[2] HDK ® N20 (origin Wacker Chemie AG Germany)
[3] 51941 A Origin Firmenich SA, Switzerland
[4] Capsul ® (origin Ingredion)
[5] Glucidex ®18DE (origin: Roquette)
[6] Sigma Aldrich
[7] Sigma Aldrich 5) Glucidex®18DE (origin: Roquette)
6) Sigma Aldrich
7) Sigma Aldrich The release of volatile orange oil after dissolution of sample B, sample Y and sample Z in water at pH=5 was monitored with a portable photoionization detector (Model Tiger, IonScience) as explained in example 4.

Figure 3:
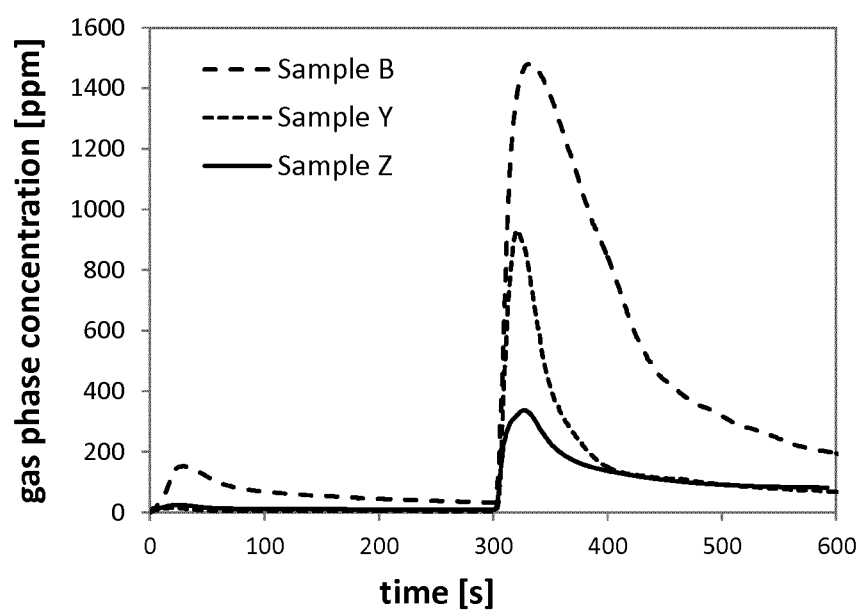
FIG. 3 represents experimental release curves of samples B, Y, and Z in an aqueous buffer solution at pH 5.

Results are shown on FIG. 3.

One can conclude from this example that spray-dried granules comprising $CaCO_3$ particles in the present invention (sample B) show a boost of flavor release under acidic pH compared to samples outside the scope of the invention.

Example 6

Olfactive Performance in Antiperspirant Deodorant Application

Sensory test have been carried out in antiperspirant deodorant (AP/Deo) application using the granules according to the invention (sample C)

Sample C has been prepared by the sample protocol as defined in example 1.

TABLE 9

Composition of powdered composition (sample C)

| Compound | Amount (%) |
|---|---|
| $CaCO_3$ [1] | 0.57 |
| Perfume A [2] | 18.50 |
| Maltodextrin 18DE [3] | 75.61 |
| $NaHCO_3$ [4] | 0.46 |
| $Na_2CO_3$ [5] | 0.03 |
| Water | 4.83 |
| | 100.00 |

[1] Firmenich SA, Switzerland
[2] See table 9a
[3] Glucidex ®18DE (origin: Roquette)
[4] Origin: Sigma Aldrich
[5] Origin: Sigma Aldrich 5) Origin: Sigma Aldrich TABLE 9a Composition of perfume A

| Component | % |
|---|---|
| ACÉTATE DE 4-(1,1-DIMÉTHYLÉTHYL)-1-CYCLOHEXYLE [1] | 14.5 |
| LINALOL BJ | 10.5 |
| LILIAL ® [2] | 10.0 |
| ISO E SUPER [3] | 10.0 |
| CITRONELLYL NITRILE | 9.0 |
| DIPHENYLOXYDE | 6.5 |
| ISOBORNYL ACETATE | 6.0 |
| BETA IONONE | 6.0 |
| TRICYCLO[5.2.1.0~2,6~]DEC-3-EN-8-YL ACETATE (A) + TRICYCLO[5.2.1.0~2,6~]DEC-4-EN-8-YL ACETATE (B) [4] | 5.5 |
| ETHER MT | 4.0 |
| HEDIONE ® [5] | 4.0 |
| GERANIOL 60 | 3.0 |
| CITRAL | 2.5 |
| ALDEHYDE C 10 | 2.5 |
| ALLYL HEPTANOATE | 2.5 |
| ETHYL METHYL-2-BUTYRATE | 1.5 |
| GERANYL ACETATE | 1.0 |
| 2,4-DIMETHYL-3-CYCLOHEXENE-1-CARBALDEHYDE [6] | 1.0 |

[1] Firmenich SA, Switzerland
[2] 3-(4-tert-butylphenyl)-2-methylpropanal, Givaudan SA, Vernier, Switzerland
[3] 1-(octahydro-2,3,8,8-tetramethyl-2-naphtalenyl)-1-ethanone, International Flavors & Fragrances, USA
[4] Firmenich SA, Switzerland
[5] Methyl dihydrojasmonate, Firmenich SA, Switzerland
[6] Firmenich SA, Switzerland Sample C has been introduced in AP/Deo stick formulation (see table 10).

TABLE 10

AP/Deo Stick formulation

| Compound | Amount (%) |
|---|---|
| Cyclomethicone [1] | 53.78 |
| Stearyl Alcohol [2] | 20.53 |
| PPG-14 Butyl Ether [3] | 1.96 |
| Hydrogenated Castor Oil [4] | 0.98 |
| Aluminium Zirconium tetrachlorohydrex-Gly [5] | 19.56 |

TABLE 10-continued

AP/Deo Stick formulation

| Compound | Amount (%) |
|---|---|
| Sample C | 3.2 |
| | 100.00 |

1) Dow Corning 345 Fluid (origin: Dow Corning)
2) Lanette ®18 (origin: BASF)
3) Tegosoft ® PBE (origin: Evonik)
4) Cutina ® HR (origin: BASF)
5) Summit AZP-908 (aluminium zirconium tetrachlorohydration glycin; origin: SummitReheis)
6) Perfume (origin: Firmenich SA, Switzerland)

Sensory Tests in Application

Sensory tests were performed by applying the antiperspirant bases on blotters.

Protocol for AP Sticks:

Weigh 0.15 g of stick on blotter paper.
Prepare 3 blotters per sample to evaluate
Store 1 hour the blotters at 37° C. on heat plate.
Evaluate and compare the global intensity of the fragrance before and after humidification with water pH=5 sprayed on blotters.

Results:

After 3 months of storage at 45° C., the AP/Stick sample was evaluated. A strong boost of perfume was smelt after humidification of the blotter when compared to the dry sample, with a difference in intensity $\Delta_{after-before\ water}=7$ on a 1-10 scale.

Example 7

Powder Soft Drink Beverage Comprising the Powdered Composition as Defined in the Present Invention The following powder soft drink beverage composition is prepared. 120 g of this formulation is suitable to produce 1 l of beverage.

TABLE 11

Soft drink beverage composition comprising the powdered composition of the present invention

| Compound | Amount (%) |
|---|---|
| Citric acid anhydrous E330 1) | 3.33 |
| Sugar (castor sugar) 2) | 95.7 |
| Tri-Calcium Phosphate 3) | 0.16 |
| CMC Blanose 7HOF (sodium) E466 4) | 0.4 |
| Tri-sodium citrate dehydrate E331 5) | 0.17 |
| Neutral clouding agent 6) | 0.08 |
| Sunset Yellow Dualake E110 7) | 0.05 |
| Tartrazine Yellow 5 Lake 40 E102 8) | 0.02 |
| Sample B Flavoring ingredient | 0.09 |
| | 100 |

1) Sigma Aldrich
2) Sugro AG
3) Sigma Aldrich
4) Ashland Europe
5) Sigma Aldrich
6) Firmenich SA
7) Sensient Food Colors Europe
8) Sensient Food Colors Europe

The invention claimed is:

1. A process for releasing a burst of hydrophobic active ingredient intensity comprising a step consisting of contacting a powdered composition with a medium having a pH≤7, said powdered composition comprising spray-dried granules made of:
    a water soluble polymer matrix,
    an oil phase comprising a hydrophobic active ingredient dispersed in said matrix, wherein said oil is at least partly not encapsulated in the matrix, and
    carbonate particles, wherein the carbonate particles are selected from the group consisting of calcium carbonate, magnesium carbonate and mixtures thereof;
    wherein the spray-dried granules are obtained by a process comprising the steps of:
        a) adding a solution of a water-soluble polymer to a Pickering emulsion, wherein the Pickering emulsion comprises
            i. a non-encapsulated oil phase comprising a hydrophobic active ingredient,
            ii. carbonate particles;
            iii. water; and
            iv. an acid chosen in the group consisting of ascorbic acid, citric acid, lactic acid, tannic acid, tartaric acid, malic acid, hydrochloric acid and mixtures thereof;
        b) optionally, adding a core-shell microcapsule slurry to the emulsion of step a), said slurry comprising microcapsules having a polymeric shell and a core comprising an encapsulated oil; and
    spray-drying the emulsion obtained in step a) or b) to obtain a powdered composition;
    wherein the Pickering emulsion is formed at a pH>6.

2. The process according to claim 1, wherein the totality of the oil phase is freely dispersed in the matrix.

3. The process according to claim 1, wherein the oil phase further comprises at least one part encapsulated in core-shell microcapsules.

4. The process according to claim 1, wherein the acid is present in an amount between 0.001:1 to 0.5:1 relative to the amount of carbonate particles.

5. The process according to claim 1, wherein the granules are free from molecular emulsifiers.

6. The process according to claim 1, wherein the water soluble polymer matrix is selected from the group consisting of maltodextrin, inulin, corn syrup, dextrin, and mixtures thereof.

7. The process according to claim 1, wherein the carbonate particles are used in an amount between 0.1 and 30% by weight based on the total weight of the powdered composition.

8. The process according to claim 1, wherein a weight ratio between carbonate particles to hydrophobic active ingredient is between 1:1 and 1:30.

9. The process according to claim 1, wherein no molecular emulsifier susceptible to form and/or stabilize the oil-in-water emulsion is added at any stage of the process.

10. A composition in the form of a antiperspirant or deodorant composition comprising:
    an antiperspirant or deodorant active ingredient, and
    a powdered composition as defined in claim 1, wherein the hydrophobic active ingredient comprises a perfume.

11. A composition in the form of a powder soft drink beverage composition comprising:
- an acidifying ingredient, and
- a dry flavouring ingredient comprising the powdered composition as defined in claim 1, wherein the hydrophobic active ingredient comprises a flavour.

12. The process according to claim 1, wherein the oil phase of the granules comprise a perfume or a flavor.

13. The process according to claim 4, wherein the acid is present in an amount from 0.001:1 to 0.05:1 relative to the amount of carbonate particles.

14. The process according to claim 8, wherein the weight ratio between carbonate particles to hydrophobic active ingredient is between 1:1.5 and 1:20.

\* \* \* \* \*